United States Patent [19]

Michalowicz

[11] Patent Number: 4,754,039
[45] Date of Patent: Jun. 28, 1988

[54] PROCESS FOR THE PREPARATION OF PYRIDINE-2,3-DICARBOXYLIC ACID

[75] Inventor: William Michalowicz, Flemington, Pa.

[73] Assignee: Ruetgers-Nease Chemical Co., Inc., State College, Pa.

[21] Appl. No.: 824,080

[22] Filed: Jan. 30, 1986

[51] Int. Cl.$^4$ .......................................... C07D 213/807
[52] U.S. Cl. ................................................... 546/320
[58] Field of Search ........................................ 546/320

[56] References Cited

U.S. PATENT DOCUMENTS

| | | | |
|---|---|---|---|
| 2,371,691 | 3/1945 | Hawkinson et al. | 546/5 |
| 2,522,163 | 9/1950 | Cislak et al. | 546/320 |
| 2,964,529 | 12/1960 | Sturrock et al. | 546/320 |
| 4,549,024 | 11/1985 | Orth et al. | 546/320 |

FOREIGN PATENT DOCUMENTS

| | | |
|---|---|---|
| 0024197 | 7/1981 | European Pat. Off. . |
| 0034943 | 9/1981 | European Pat. Off. . |
| 945147 | 7/1956 | Fed. Rep. of Germany . |
| 1010524 | 4/1957 | Fed. Rep. of Germany . |
| 3150005 | 6/1983 | Fed. Rep. of Germany . |
| 3345223 | 6/1985 | Fed. Rep. of Germany . |

Primary Examiner—Richard A. Schwartz
Assistant Examiner—Dale A. Bjorkman
Attorney, Agent, or Firm—Woodcock Washburn Kurtz Mackiewicz & Norris

[57] ABSTRACT

Pyridine-2,3-dicarboxylic acid can be prepared by oxidizing quinoline with a chlorate salt in an aqueous acidic medium. The oxidation can be conducted in the presence of cupric ions generated from an acid-soluble cupric compound.

8 Claims, No Drawings

PROCESS FOR THE PREPARATION OF PYRIDINE-2,3-DICARBOXYLIC ACID

BACKGROUND OF THE INVENTION

This invention is directed to a process for preparing pyridine-2,3-dicarboxylic acid by the oxidation of quinoline. The invention is more particularly directed to a process for preparing that acid by oxidizing quinoline with a chlorate salt in an aqueous acid medium. The acid is useful as an intermediate in the preparation of various herbicides and pharmaceuticals, and in the preparation of dye intermediates.

Pyridine-2,3-dicarboxylic acid, also known as quinolinic acid, has been prepared from quinoline and its derivatives by well established means. The chemical processes heretofore used, however, have not been economical on a commercial scale because of low yield, high raw material cost, or severe process conditions necessary to achieve a commercially acceptable rate or yield.

The oxidation of quinoline or a quinoline derivative by common chemical oxidants is well known in the art. Oxidation by potassium permanganate is disclosed, for example, in Current Sci. 13 206–7, 1944; Ber. 65B, 11–13, 1932; Anal. Chem. 23 535–6, 1951; Chemical Abstracts 50 9996, 52 11847d, 55 530e 56 5807i, 99 141522c. Oxidation by manganese dioxide is shown in U.S. Patent 2,392,437 and U.K. Pat. No. 596,230. Chromic and lead oxides have also been employed (J.A.C.S. 70, 3827–30, 1948; German Pat. No. 1,071,085; Chemical Abstract 47 5232c).

The oxidation of quinoline and quinoline derivatives by nitric acid or nitrogen oxides, in either liquid or vapor phase, has also been extensively developed. See, for example, U.S. Pat. Nos. 2,396,457; 2,475,969; 2,505,568; 2,513,251; 2,513,099; Ger. Nos. 912, 216; 1.133,714; 1.161,563; and Chemical Abstract 44 3494e, 50 9403e. The process conditions required in these procedures, however, are normally so severe that nicotinic acid is the main or only product.

Quinoline and quinoline derivatives have also been oxidized by ozonation, but the products require further chemical oxidation to produce pyridine dicarboxylic acid. Such procedures are disclosed in J.A.C.S. 71 3020, 1949; U.S. Pat. No. 2,964,529; CA 69 35876s; CA 88 225606; and CA 69 2825w.

The electrochemical oxidation of quinoline and its derivatives has been successfully demonstrated (J.A.C.S. 68 2472–3, 1946; U.S. Pat. Nos. 2,453,701; 2,512,483; ) but the procedures have not been of commercial significance, usually because of the cost involved in operation of this complex procedure. More practical procedures, using hydrogen peroxide to oxidize quinoline in an aqueous acid medium, are shown in Eur. Pat. Appln. Nos. 024,197 and 034,943; CA 50 12057b; CA 60 15704c; and U.S. Pat. Nos. 2,371,691. Catalytic oxidations of quinoline using oxygen or air are also known (U.S. Pat. No. 3,829,432; Ger. Pat. No. 1,010,524; CA 31 5790, CA 54 2911i, CA 69 35876s).

A disubstituted quinoline has been oxidized by sodium chlorite to pyridine dicarboxylic acid, as shown in German Patent No. 945,147 (1956). U.S. Pat. No. 2,586,555 discloses the oxidation of quinoline by perchloric acid to form nicotinic acid, although it is also disclosed that pyridine dicarboxylic acid can be produced. This process, however, requires uneconomically high temperatures, despite the presence of a catalyst.

The above processes have not proven to be commercially feasible. One or more problems attending these processes are the high cost of the reagents, the severe process conditions required, low yield of product, and difficulty in isolating the product from the reaction process. As a consequence, pyridine-2,3-dicarboxylic acid is commercially available only at high cost.

A process which heretofore has been of some commercial significance is that disclosed in German Pat. No. 3,150,005. In that process, a quinoline which must contain substitution in the non-heterocyclic ring by an activating group is oxidized by a chlorate salt. The practical use of this process is limited by the commercial availability of activated quinolines. Such activated quinolines that are commercially available are the hydroxyquinolines, which are prepared by sulfonation of quinoline with subsequent caustic fusion and hydrolysis of the fusion products.

Consequently, there remains a need for a commercially practical process for the preparation of pyridine dicarboxylic acid from more readily available starting compounds.

SUMMARY OF THE INVENTION

The present invention provides a process for preparing pyridine-2,3-dicarboxylic acid. The process comprises reacting quinoline, which contains no substitution, with a chlorate salt in an aqueous acid medium. In a preferred embodiment, the reaction is performed in the presence of a cupric compound, which increases the yield of the derived product.

It has been found that quinoline can be oxidized with a chlorate salt in an acid medium without the need to first activate the quinoline by introducing the presence of substituent groups as specified in German Pat. No. 3,150,005. By the present process, pyridine-2,3-dicarboxylic acid is prepared at commercially reasonable process conditions in practical yields.

DETAILED DESCRIPTION OF THE INVENTION

According to the process of the present invention, quinoline having no substitution, and particularly no activating group substitution, can be oxidized to pyridine-2,3-dicarboxylic acid in an aqueous reaction medium which has been acidified by the addition of a mineral acid. Quinoline, unsubstituted as used in the present invention, is more readily available than are the substituted quinolines of German Pat. No. 3,150,005, making the present process more commercially attractive. By "activating group", it is meant the election-donating groups which are generally known to promote the further electrophilic substitution of an aromatic ring.

As those skilled in the art will recognize, such commercially important aspects as the rate at which the reaction proceeds and the product yield of the reaction will depend in part on several reaction parameters. In the conduct of the present reaction process, those parameters include the relative amounts of chlorate and quinoline, the ratio of acid equivalents to quinoline, and the concentrations of acid and quinoline in the reaction medium.

The theoretical molar ratio of chlorate to quinoline necessary for complete oxidation to pyridine-2,3-dicarboxylic acid is 3:1. Although a ratio of less than 3 can be employed, it is preferred to operate at the theoretical ratio and most preferred to operate at an excess of chlorate. Although a larger excess can be used, a molar excess greater than about 30% (that is, about 3.9:1) confers little additional benefit. A molar excess of about 17% to 25% is preferred.

The chlorate can be provided in the form of any salt which is compatible with the other reagents. Examples are the alkali metal salts, which are preferred, the alkaline earth metal salts, and ammonium salt. In general, sodium chlorate is particularly preferred because of its ready availability and high solubility in water.

The acids which can be added to the reaction medium are any of the common mineral acids. Exemplary of preferred acids are sulfuric acid, nitric acid, phosphoric acid, hydrochloric acid, and perchloric acid. Mixtures of these acids can also be used. Most preferred are sulfuric acid and nitric acid. The choice of mineral acid and chlorate salt will depend on relative compatibility in the reaction system. For example, to avoid the formation of an insoluble sulfate precipitate, an alkaline earth salt should generally not be chosen when sulfuric acid is present.

In the conduct of this invention, it is preferred that sufficient acid be present to provide an acid:quinoline equivalent ratio of from about 0.6 to 6.0. Most preferred, for obtaining the best yield of product are ratios in the range of about 1.5 to 2.1. The overall acid concentration is from about 1.2–12.8 acid equivalents per liter of water, although the higher concentrations within this range, while promoting the oxidation reaction rate, lead to some reduction in yield. It has been found that in a reaction procedure in which all the reactants are combined and then brought to the reaction temperature, an acid concentration of about 1.5 to 3.5 equivalents of acid per liter of total water in the reaction mixture provides a very acceptable balance between yield and reaction rate. In a variation of reaction technique, where the chlorate oxidant is added to the other reactants, which have been pre-mixed and brought to reaction temperature, an acid concentration of about 4.0 to 6.2 equivalents per liter is preferred.

The quinoline concentration of the reaction mixture, defined as the weight percent of quinoline based on the total weight of the reaction charge, is from about 4–13%, preferably about 5.8–11.0%. At the lower concentrations within this range, the reaction time required for completion of the reaction is greater than that required at the higher concentration, but the yield of product, based on quinoline charge, is also greater, the yield being inversely proportional to the concentration. The most preferred concentration range, taking into account these factors, is about 7.8 to 8.5%.

Under the reaction conditions described herein, chlorate will oxidize quinoline to pyridine-2,3-dicarboxylic acid to provide a product yield, based on the quinoline charge, of about 24–26%. The unoxidized quinoline can be recovered, although some is involved in tar formation. In a most preferred embodiment of the invention, in which the chlorate oxidation of quinoline is performed in the presence of a cupric compound, the isolated yield of quinolinic acid can be raised to about 55% to 62%, based on the original charge of quinoline. The cupric ions generated by the dissolution of the compound combine with and precipitate the pyridine-2,3-dicarboxylic acid as it forms, thus protecting it from degradative side-reactions. The resulting copper salt of pyridine-2,3-dicarboxylic acid can be resolved into the acid itself by known methods, such as digestion with caustic soda or sulfide.

The copper salt of pyridine-2,3-dicarboxylic acid can exist as either a 1:1 or 1:2 (copper:acid) salt. In the conduct of the reaction, sufficient cupric compound is added to provide a copper:quinoline molar ratio of from about 0.5:1 to 2:1, but copper in excess of a 1:1 molar ratio provides only slightly higher product yield and purity. The use of a copper:quinoline ratio lower than about 0.7:1 gives slightly lower yields and purity of product. The preferred molar ratio range is from about 0.75:1 to 1.0:1.

Any material that contains copper in the cupric state, is acid soluble, and does not contain excess organic matter that is oxidizable by chlorate can be used as the source of copper. Copper metal itself can also be used, but it must first be oxidized to the cupric state by standard means, as for example by treatment with sulfuric acid-chlorate, nitric acid, or sulfuric acid-hydrogen peroxide. Cupric salts and cupric oxide are preferred, with the latter being most preferred because it is soluble in either nitric or sulfuric acid and does not introduce any additional anions.

In the practice of the invention, the reactants, including the acid, and water are charged to an appropriate reaction vessel and heated, usually with mixing, to the reaction temperature. As the reaction is initiated, a strong exotherm becomes apparent; accordingly, adequate cooling capacity for the reaction system is recommended to keep the temperature within the desired range and the reaction under control. In a variation of this procedure, the water, acid, and all reactants except the chlorate salt are charged to the vessel. The charge is mixed and heated, and the chlorate salt added when the charge reaches the desired temperature at which to run the reaction. In general, the reaction is performed at a temperature of from about 70° C. to 125° C. The reaction can be performed at atmospheric pressure, at the elevated pressures provided autogenously by reaction temperatures above 100° C., or under a pressure of inert gas. As those skilled in the art will recognize, the reaction time will depend on such factors as temperature and reactant concentration, but generally from about 10–20 hours are required to complete the reaction.

During the reaction, an inert gas, such as nitrogen or carbon dioxide, preferably is swept through the reactor to remove any chlorine dioxide that might be generated. The build-up of chlorine dioxide in the vapor space above the reaction mixture should generally be avoided to eliminate the risk of explosion.

As an example of one embodiment of the present process, the reaction components are all charged to a reactor and the temperature is raised to reaction temperature (99°–103° C.). After an induction period of from 1 to 5 hours, depending on the composition of the charge, an exotherm becomes apparent and gas evolution increases substantially. The reaction temperature is maintained at 99°–101° C. by appropriate cooling. A blue suspension forms and becomes heavier with continued reaction. A standard antifoaming agent can be added. At the completion of the reaction, indicated by the substantial reduction or cessation of gas evolution, the reaction mass is allowed to cool and the product is isolated by filtration. Total reaction time of 10–17 hours is generally sufficient.

In another example of a preferred embodiment of the process, a sodium chlorate solution is added in small increments to a mixture of the other components, including copper oxide, which has been previously mixed and heated to reaction temperature (99°–101° C.). The acid concentration in the mixture is about 5 equivalents of acid per liter. The total chlorate addition will provide a chlorate molar excess of about 18% relative to the quinoline present. An exotherm becomes apparent after 6–8% of the chlorate has been added, and soon thereafter a suspension of copper quinolinate develops. Total chlorate addition is completed in 2–4 hours with total reaction time of 10–12 hours. The product, crude copper salt of pyridine-2,3-dicarboxylic acid, is isolated by filtration.

The crude copper salt of pyridine dicarboxylic acid is obtained in 72% to 82% of theory. This copper salt is resolved into the disodium salt of pyridine-2,3-dicarboxylic acid by digestion in caustic soda, with the copper oxide being regenerated. The copper oxide is removed by filtration and the disodium salt is acidified to obtain the free acid. The product yield and purity are slightly increased if formaldehyde is used in addition to caustic soda to treat the copper salt.

The following specific examples illustrate various embodiments of the present invention. In the examples, the quinoline used is 94% by weight pure, containing 6% by weight isoquinoline and other nitrogenous bases, all of which are oxidizable bases; the product yield is based on the actual quinoline present.

EXAMPLE 1

The following ingredients were charged to a reactor:
Water—267 g
Copper sulfate pentahydrate—67.4 g, 0.27 mole
Quinoline—34.8 g, 0.27 mole
97% Sulfuric acid—33.8 g, 0.335 mole
Sodium chlorate—101.2 g, 0.95 mole
The reaction charge was stirred at 98°–100° C. for a total of 17 hours while a purge stream of nitrogen (40 ml. per minute) was passed through the reactor. After 7.5 hours, a blue suspension developed and became heavier with time. The suspension was filtered and the product dried to yield 50.1 g of crude copper salt of pyridine dicarboxylic acid (81% yield).

The free acid was recovered from the crude copper salt by charging to a reaction vessel:
Crude copper salt—50.1 g
Water—125g
50% Caustic soda—50 g
Paraformaldehyde—3.8 g
The charge was maintained at 70° C. for 1 hour, then filtered. The filtrate was acidified with 70% nitric acid (53 g) to a pH of 1.1, resulting in precipitation of the pyridine-2,3-dicarboxylic acid. When precipitation was complete, the acid was isolated and dried to yield 26.6 g, m.p. 188° C. (62.8% based on the originally charged quinoline).

EXAMPLE 2

The following ingredients were charged to a reactor:
Water—197.7 g
Copper sulfate pentahydrate—67.4 g, 0.27 mole
Quinoline—34.8 g, 0.27 mole
97% Sulfuric acid—27.2 g, 0.27 mole
Sodium chlorate—1012 g, 0.95 mole
The reaction was conducted as in Example 1 for a total of 17 hours. After 3.5 hours, a blue suspension developed. The recovery procedure as in Example 1 gave 49.7 g of dried copper salt of pyridine-2,3-dicarboxylic acid, from which 26.4 g of pyridine-2,3-dicarboxylic acid were isolated, mp 186°–187° C. (62.3% yield).

EXAMPLE 3

The following ingredients were charged to a reactor:
Water—185 g
Copper sulfate pentahydrate—67.4 g, 0.27 mole
Quinoline—34.8 g, 0.27 mole
70% Nitric Acid—41.3 g, 0.459 mole
Sodium chlorate—101.2 g, 0.95 mole
The reaction was conducted as in Example 1 for 17 hours. After 3.5 hours, an exotherm developed and a blue suspension became apparent. The recovery procedure as in ample 1 gave the copper salt (47.2 g) from which pyridine-2,3-dicarboxylic acid was isolated (25.5 g; mp 188° C.) in 60.2% yield.

EXAMPLE 4

The following ingredients were charged to a reactor:
Copper powder—17.1 g, 0.27 mole
Water—197 g
70% Nitric Acid—72.9 g, 0.81 mole
After the copper metal had dissolved, the system was purged with nitrogen to remove residual nitric oxide. The system was further charged with:
70% Nitric acid—24.3 g, 0.27 mole
Quinoline—34.8 g, 0.27 mole
Sodium chlorate—107.6 g, 1.01 mole
The resulting reaction mixture was maintained at 100° C. for a total of 10 hours. After an initial 3-hour induction period, an exotherm developed followed by formation of a blue suspension. The recovery procedure as in Example 1 gave 45.5 g copper salt from which 25.0 g (mp 185° C.; 59% yield) of pyridine-2,3-dicarboxylic acid were isolated.

EXAMPLE 5

The following ingredients were charged to a reactor:
Cupric oxide—42.9 g, 0.54 mole
Water—202.9 g
97% Sulfuric acid—84.8 g, 0.84 mole
70% Nitric acid—48.6 g, 0.54 mole
Quinoline—69.6 g, 0.54 mole
The system was stirred at 100° C. while 430 g of a 50%-by-weight solution of sodium chlorate was added over a five-hour period. After two additional hours at this temperature, a blue suspension became evident. After a total reaction time of 10 hours (including the chlorate addition), the recovery procedure as in Example 1 gave 95.3 g copper salt from which 50.6 g (mp 187° C., 59.7%) of pyridine-2,3-dicarboxylic acid were isolated.

EXAMPLE 6

The following ingredients were charged to a reactor:
Water—90 g
Copper sulfate pentahydrate—67.4 g, 0.27 mole
70% Nitric acid—25.5 g, 0.283 mole
Quinoline—34.8 g, 0.27 mole
Sodium chlorate—101.2 g, 0.95 mole
The mixture was stirred at 98°–100° C. for a total of 17 hours. After 2.75 hours, an exotherm developed and soon thereafter a blue suspension was evident. The recovery procedure as in Example 1 gave 49.1g of copper salt, processed to 21.4 g (mp 184°–185° C.; 50.5% yield) of pyridine-2,3-dicarboxylic acid.

EXAMPLE 7

The following ingredients were charged to a reactor:
Water—174 g
Copper sulfate pentahydrate—134.8 g, 0.54 mole
97% Sulfuric acid—33.4 g, 0.335 mole
Quinoline—34.8 g, 0.27 mole
Sodium chlorate—101.2 g, 0.95 mole The reaction mixture was stirred at 98°–100° C. for 17 hours. The recovery procedure of Example 1 gave 49.3 g of copper salt, processed 25.7 g (mp 185° C.; 61.6% yield) of pyridine-2,3-dicarboxylic acid.

EXAMPLE 8

The following ingredients were charged to a reactor:
Water—201 g
Copper sulfate pentahydrate—33.7 g, 0;135 mole
70% Nitric acid—41.3 g, 0.459 mole
Quinoline—34.8 g, 0.27 mole
Sodium chlorate—101.2 g, 0.95 mole The reaction mixture was stirred at 98°–100° C. for 17 hours. After 2.75 hours an exotherm developed and a blue suspension formed soon thereafter. The recovery procedure of Example 1 gave 46.1 g of copper salt from which 24.5 g (mp 187° C.; 57.8% yield) of pyridine-2,3-dicarboxylic acid were isolated.

EXAMPLE 9

The following ingredients were charged to a reactor:
Water—333 g
97% Sulfuric acid—34.1 g, 0.335 mole
Quinoline—34.8%, 0.27 mole
Sodium chlorate—107.6 g, 1.01 mole The mixture was stirred for 17 hours at 100°–101° C., after which it was cooled and the pH adjusted to 4.5 with 50% caustic soda (53.7 g). Activated carbon (2 g) was added and the system was filtered. The filtrate was acidified with 70% nitric acid (29.9 g) to a pH 1.1, resulting in the precipitation of the final product. After precipitation was completed, isolation of the pyridine-2,3-dicarboxylic acid provided 11.0 g (mp 187° C.; 25.9% yield).

EXAMPLE 10

The following ingredients were charged to a reactor:
Water—181 g
Copper sulfate pentahydrate—57.3 g, 0.405 mole
70–72% Perchloric acid—57.3 g, 0.405 mole
Quinoline—34.8 g, 0.27 mole
Sodium chlorate—101.2 g, 0.95 mole The reaction mixture was stirred for 17 hours at 99°–100° C. The recovery procedure of Example 1 gave 48.1 g of copper salt, and 24.2 g (mp 187°–188° C.; 57.1% yield) of pyridine-2,3-dicarboxylic acid were isolated.

EXAMPLE 11

The following ingredients were charged to a reactor:
Water—156 g
Copper sulfate pentahydrate—67.4 g, 0.27 mole
37% Hydrochloric acid—66.1g, 0.67 mole
Quinoline—34.8 g, 0.27 mole
Sodium chlorate—101.2 g, 0.95 mole The reaction mixture was stirred at 98°–110° C. for 17 hours. The recovery procedure of Example 1 gave 35.0 g of copper salt from which 18.5 g (mp 187°–188° C.; 43.6 % yield) of pyridine-2,3-dicarboxylic acid were isolated.

EXAMPLE 12

The following ingredients were charged to a reactor:
Water—76 g
Copper sulfate pentahydrate—67.4 g, 0.27 mole
97% Sulfuric acid—81.7g, 0.81 mole
Quinoline—34.8 g, 0.27 mole The mixture was stirred and heated to a temperature of 98°–100° C., after which 206 g of an approximately 50% solution of sodium chlorate was added, with stirring, over an 8-hour period. Reaction continued for a total of 17 hours. The recovery procedure of Example 1 gave 49.9 g of copper salt from which 21.3 g (mp 187°–188° C.; 50.3% yield) of pyridine-2,3-dicarboxylic acid were isolated.

EXAMPLE 13

The following ingredients were charged to a reactor:
Water—154 g
Copper sulfate pentahydrate 67.4 g, 0.27 mole
70% Nitric acid—145.8 g, 1.62 mole
Quinoline—34.8 g, 0.27 mole
Sodium chlorate—107.6 g, 1.01 mole The reaction mixture was stirred at 68°–70° C. for 17 hours. The recovery procedure of Example 1 gave the copper salt, 18.8 g, from which 8.7 g (mp 187° C.; 20.5% yield) pyridine-2,3-dicarboxylic acid were isolated.

EXAMPLE 14

The following ingredients were charged to a laboratory autoclave with glass liner:
Water—150 g
Copper sulfate pentahydrate—13.5 g, 0.054 mole
97% Sulfuric acid—9.4 g,—0.093 mole
Quinoline—6.9 g, 0.054 mole
Sodium chlorate—18.1 g, 0.17 mole The charge was heated to 100° C., subjected to nitrogen pressure (15 psig), and then heated under that pressure until the temperature reached 125° C. The temperature was maintained at 125°–127° C. for 50 minutes, after which time a rapid exotherm ensued, raising the temperature to 140° C. and the pressure to 100 psig. At the end of the reaction period, the autoclave was cooled. The recovery procedure of Example 1 provided 6.1 g of copper salt from which 3.0 g (mp 186°–187° C.; 35.4% yield) of pyridine-2,3-dicarboxylic acid were isolated.

EXAMPLE 15

The following ingredients were charged to a reactor:
Water—1322 g
Cupric oxide—250.6 g, 3.15 mole
97% Sulfuric acid—954.7 g, 9.45 mole
Quinoline—406 g, 3.15 mole
70% Nitric acid—283.5 g, 3.15 mole The mixture was stirred and heated to 100° C. When this temperature was reached, a nitrogen purge sweep was started while 2516 grams of a 50% solution of sodium chlorate in water was added over a 7.75-hour period. A blue suspension was evident after 22% of the chlorate had been added. An antifoam agent was added towards the end of the chlorate addition. After a total reaction time of 12 hours, the recovery procedure of Example 1 gave the copper salt, 634.2 g, from which 306.4 g (mp 186° C.; 62.0% yield) of pyridine-2,2-dicarboxylic acid were isolated.

EXAMPLE 16

The following ingredients were charged to a 300 gallon glass lined reactor
Water—795 lbs.
35.9% Nitric acid, 426.8 lbs., 2.43 lb. moles
Copper sulfate pentahydrate—357.3 lbs., 1.43 lb. mole
Quinoline—185 lbs., 1.43 lb. moles
Sodium chlorate—569 lbs., 5.34 lb. moles The reaction mass was stirred under a nitrogen purge sweep at 100° C. After 5 hours, an exotherm became evident which persisted for 4 hours. Temperature was maintained at 100–104° C. by appropriate cooling. After a total reaction time of 17 hours, a wet cake of copper quinoline (271.9 lbs. on dry basis) was obtained which was resolved into pyridine-2,2-dicarboxylic acid by the procedure of Example 1 (without formaldehyde) to give 124.0 lbs. of product (55.1% yield, assay 98.8%).

I claim:

1. A process for the preparation of pyridine-2,3-dicarboxylic acid comprising reacting quinoline with a chlorate salt in an aqueous acid medium at a temperature of about 70° C. to 125° C., wherein the equivalent ratio of acid to chlorate salt to quinoline is at least about 3.0, and the acid concentration is from about 1.5 to about 6.2 acid equivalents per liter of water.

2. A process of claim 1 in which the chlorate salt is an alkali metal salt.

3. A process of claim 1 in which the chlorate salt is sodium chlorate.

4. A process of claim 1 in which the reacting step is performed in the presence of a cupric compound.

5. A process of claim 4 additionally comprising the step of treating the product of the reacting step with caustic soda and formaldehyde.

6. A process of claim 4 in which the cupric compound is present in an amount sufficient to provide a copper/quinoline molar ratio of from about 0.5 to about 2.0.

7. A process of claim 1 in which the aqueous medium is acidified with sulfuric acid, nitric acid, hydrochloric acid, perchloric acid, phosphoric acid, or a mixture of two or more of these.

8. A process of claim 6 in which the cupric compound is cubic oxide.

* * * * *

UNITED STATES PATENT AND TRADEMARK OFFICE
CERTIFICATE OF CORRECTION

PATENT NO. : 4,754,039
DATED : June 28, 1988
INVENTOR(S) : William Michalowicz

It is certified that error appears in the above-identified patent and that said Letters Patent is hereby corrected as shown below:

Column 5, line 63, "1012" should read --101.2"

In claim 1 at column 10, line 1, after "acid to" insert
 --quinoline is from about 0.6 to about 6.0, the
 molar ratio of--

Signed and Sealed this

Sixth Day of December, 1988

Attest:

DONALD J. QUIGG

Attesting Officer

Commissioner of Patents and Trademarks